(12) United States Patent
Nikawa et al.

(10) Patent No.: US 9,278,107 B2
(45) Date of Patent: Mar. 8, 2016

(54) ANTIBACTERIAL AGENT COMPOSITION AND ANTIVIRAL AGENT COMPOSITION COMPRISING SILICON-CONTAINING COMPOUND; ANTIBACTERIALIZING METHOD, CLEANING/MOUTH RINSING METHOD; METHOD FOR FIXING ANTIBACTERIAL AGENT AND ANTIVIRAL AGENT

(75) Inventors: Hiroki Nikawa, Hiroshima (JP); Hironori Takeda, Fukuyama (JP); Toshio Kakihara, Fukuyama (JP); Takemasa Sakaguchi, Hiroshima (JP)

(73) Assignee: Hiroshima University, Hiroshima (JP)

( * ) Notice: Subject to any disclaimer, the term of this patent is extended or adjusted under 35 U.S.C. 154(b) by 90 days.

(21) Appl. No.: 13/142,088

(22) PCT Filed: Nov. 5, 2009

(86) PCT No.: PCT/JP2009/068929
§ 371 (c)(1),
(2), (4) Date: Aug. 12, 2011

(87) PCT Pub. No.: WO2010/073825
PCT Pub. Date: Jul. 1, 2010

(65) Prior Publication Data
US 2011/0293542 A1 Dec. 1, 2011

(30) Foreign Application Priority Data

Dec. 25, 2008 (JP) .................................. 2008-329036
Sep. 4, 2009 (JP) .................................. 2009-205296
Oct. 7, 2009 (JP) .................................. 2009-233013

(51) Int. Cl.
*A01N 55/10* (2006.01)
*A01N 33/12* (2006.01)
(Continued)

(52) U.S. Cl.
CPC .............. *A61K 31/695* (2013.01); *A01N 33/12* (2013.01); *A01N 55/00* (2013.01); *C07F 7/1836* (2013.01); *C11D 3/3742* (2013.01); *C11D 3/48* (2013.01)

(58) Field of Classification Search
None
See application file for complete search history.

(56) References Cited

U.S. PATENT DOCUMENTS 4,005,028 A * 1/1977 Heckert et al. ................ 510/180
4,511,486 A * 4/1985 Shah .............................. 134/42
(Continued)

FOREIGN PATENT DOCUMENTS

CN 1792158 A 6/2006
CN 102105062 A 6/2011
(Continued)

OTHER PUBLICATIONS

"Synthesis, Surface Active Properties and Antimicrobial Activity of New Bis Quaternary Ammonium Compounds" by Diz et al., J. Chem. Soc. Perkin Trans. 2, 1871-76 (1994).*
(Continued)

*Primary Examiner* — Theodore R West
(74) *Attorney, Agent, or Firm* — Renner, Kenner; Arthur M. Reginelli

(57) ABSTRACT

Disclosed is an antibacterial agent composition which is highly safe and has excellent antibacterial abilities, by using a silicon-containing compound that is obtained by a specific manufacturing method. The antibacterial agent composition has a more stable antibacterial component, and is capable of imparting antibacterial abilities to teeth, while being also capable of cleaning an article or the mouth. Also disclosed are: an antiviral agent composition which is highly safe and has excellent virus deactivation abilities; an antibacterializing method, a cleaning/mouth rinsing method, each using the antibacterial agent composition or the antiviral agent composition; and a method for fixing an antibacterial agent or an antiviral agent. The antibacterial agent composition may contain a silicon-containing compound which is represented by general formula (1) and obtained by reacting a specific triethoxysilyl compound in an ethanol solvent.

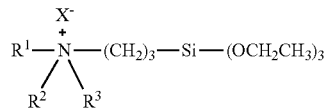

(1)

11 Claims, 3 Drawing Sheets

(51) Int. Cl.
| | |
|---|---|
| *C07F 7/18* | (2006.01) |
| *A61K 31/695* | (2006.01) |
| *A01N 55/00* | (2006.01) |
| *C11D 3/37* | (2006.01) |
| *C11D 3/48* | (2006.01) |

(56) References Cited

U.S. PATENT DOCUMENTS

| | | | | |
|---|---|---|---|---|
| 4,631,297 | A * | 12/1986 | Battice et al. | 521/78 |
| 5,411,585 | A | 5/1995 | Avery et al. | |
| 5,885,951 | A * | 3/1999 | Loder | 510/340 |
| 6,663,851 | B1 | 12/2003 | Deller et al. | |
| 7,304,022 | B2 * | 12/2007 | Cheung et al. | 510/191 |
| 8,304,379 | B2 * | 11/2012 | Nikawa | 510/384 |
| 2005/0008613 | A1 | 1/2005 | Peterson et al. | |
| 2011/0172183 | A1 | 7/2011 | Nikawa | |

FOREIGN PATENT DOCUMENTS

| | | |
|---|---|---|
| DE | 199 29 845 A1 | 1/2001 |
| EP | 2 274 985 A1 | 1/2011 |
| JP | 6-505036 | 6/1994 |
| JP | A-2006-213709 A | 8/2006 |
| JP | 2007-502328 A | 2/2007 |
| JP | A-2007-502328 A | 2/2007 |
| JP | 2007-146134 A | 6/2007 |
| WO | WO9214810 | 9/1992 |
| WO | WO9903865 | 1/1999 |
| WO | WO 2006010667 A1 * | 2/2006 ............. C08G 77/26 |
| WO | WO2009013991 A1 | 1/2009 |
| WO | WO2009136561 A1 | 11/2009 |

OTHER PUBLICATIONS

The State Intellectual Property Office of the People's Republic of China (SIPO) First Office Action Notification 24 pages (Jul. 2013).
"Theory and Practice of Antiviral Finishing", Textile Dyeing and Finishing Journal, 26(3), P14-16, 3 pages (Jun. 2004).
Interaction of Infectious Viral Particles With a Quaternary Ammonium Chloride (QAC) Surface, I-Fu Tsao, Nov. 4, 1988.
Extended European Search Report for Application No. 09834629.9 (Jun. 2012).
Office Action and Machine Translation for JP2010-543968 (Apr. 2011).
Office Action and Machine Translation for JP2011-008174 (Apr. 2011).
International Search Report date of mailing Jan. 19, 2010 for International Appl. No. PCT/JP2009/068929; English translation; 3 pages.
Office Action dated Apr. 26, 2011 for JP Appl. No. JP2010-543968; English translation; 3 pages.
Office Action dated Apr. 26, 2011 for JP Appl. No. JP2011-008174; English translation; 3 pages.
Office Action of Patent Application No. 200980157494.1 dated Mar. 23, 2015, 6 pages, China Patent & Trademark Office.
The State Intellectual Property Office of the People's Republic of China (SIPO) Third Office Action Notification date of Sep. 30, 2014, 7 pages; English translation 12 pages.

* cited by examiner

ANTIBACTERIAL AGENT COMPOSITION AND ANTIVIRAL AGENT COMPOSITION COMPRISING SILICON-CONTAINING COMPOUND; ANTIBACTERIALIZING METHOD, CLEANING/MOUTH RINSING METHOD; METHOD FOR FIXING ANTIBACTERIAL AGENT AND ANTIVIRAL AGENT

TECHNICAL FIELD

The present invention generally relates to an antibacterial agent composition and an antiviral agent composition, containing a silicon-containing compound; antibacterializing method, cleaning/mouth rinsing method, using the antibacterial agent composition and a method for fixing an antibacterial agent using the antibacterial agent composition or a method for fixing an antiviral agent using the antiviral agent composition.

RELATED ART

As a concern over hygiene of daily-life environment increases, there is increasingly a demand for higher hygiene and antibacterial standards for various articles, such as tableware, eyeglasses, sinks, kitchen fixtures, toilet, toilet fixtures, bathtubs, bath-room fixtures, wash bowls, washroom fixtures, textile products and clothes. In addition, as population of our society is aging, and largely to a global pandemic of atypical influenza, there has been a strong demand for reducing the risks of infection or secondary infection significantly by simply inactivating not only eumycetes, such as bacteria or molds, but also pathogenic viruses, such as influenza virus or norovirus, and by treating antibacterial and antiviral protection on articles in our living environment, such as towels or masks.

As such trends enhance more hygiene, antibacterial and antivirus intentions, there are increasing needs for such antibacterial agents and antiviral agents that can provide even higher sterilization and pathogenic virus inactivation abilities than those of conventional antibacterial and antiviral agents. For example, Patent Documents 1-3 disclose silicon-containing compounds that can provide an antibacterial ability, describing different forms of compositions employing such compounds.

On the other hand, focusing in particular on dental materials, more denture cleaners have been used by more denture users and denture cleansers of different compositions have been used. As such, there is a need for an antibacterial agent composition that combines the ability to allow a denture to be used again after a brief cleaning process with the cleaning ability such that the antibacterial ability lasts for a long period of time.

For example, when classifying the conventional antibacterial agent compositions capable of offering such cleaning abilities by component system, they can be classified as one comprising a major component of either a peroxide, hypochlorous acid, enzyme, acid, crude drug, silver-based inorganic antibacterial agent or disinfectant, alternatively as another combining two or more components thereof. The specific composition varies in the antibacterial agent compositions belonging to the same component system. This is because if both cleaning and sterilization abilities are required for an antibacterial agent composition, such an antibacterial agent composition is often composed of a combination of compositions exerting respective effects.

In order to fulfill such requirements, for example, Patent Document 4 discloses a detergent composition with high cleaning and sterilization abilities, aimed at improving the antibacterial ability, the cleaning ability and the persistence for a cleaned article being cleaned, and having both antibacterial and cleaning abilities that can prevent denture plaques from re-forming on a denture surface while the denture is being fixed in the oral cavity in dental materials, such as implants, crowns, bridges, orthodontic brackets or dental wires, in particular, dentures; and a denture cleanser composition that can provide a denture with the antibacterial ability, in particular, without giving a denture user special burden or uncomfortable feeling.

RELATED ART DOCUMENT

Patent Document

Patent Document 1: JP-A-2007-502328
Patent Document 2: JP-A-H6-505036
Patent Document 3: JP-A-2006-213709
Patent Document 4: JP-A-2007-146134

DISCLOSURE OF THE INVENTION

Problems to be Solved by the Invention

However, as disclosed in Patent Documents 1-3, if a silicon-containing compound formed by a so-called methoxy body, such as, e.g., octadecyldimethyl(3-trimethoxysilylpropyl)ammonium chloride, is contained in a composition, many problems remain to be resolved for the composition itself since involvement of highly toxic methanol cannot be avoided during production, transportation or use. Besides, it is still uncertain whether sufficient effects can be exerted to inactivate pathogenic viruses, in particular, influenza viruses and others.

On the other hand, a silicon-containing compound of antibacterial components comprised in the detergent composition as disclosed in Patent Document 4 above provides such a stability in a solution that depends on the solvent to be dissolved and the type of surfactant to mix. Accordingly, in some cases, this can generate cloudy gelation, thereby decreasing the antibacterial ability imparting performance of the detergent composition. Moreover, to meet the increasing demands for further enhanced hygiene and antibacterial intentions, there is still a need for an antibacterial agent composition that has further improved antibacterial abilities and more persistent antibacterial abilities.

In addition, if such an antibacterial agent composition can impart disinfection/sterilization while cleaning and antibacterial abilities, it is effective for realizing more hygienic environment and preventing infection of pathogens. Patent Document 4, however, only discloses cleaning and antibacterialization of the article of the detergent composition, but does not consider whether or not the detergent composition can impart disinfection/sterilization while cleaning and antibacterial abilities.

Moreover, if such an antibacterial detergent can achieve antibacterialization of hydroxyapatite which is a principal component of the teeth in addition to cleaning and antibacterialization of the denture, it is very effective for treatment/prevention of dental caries, periodontal diseases and other dental infectious diseases and aspiration pneumonia when used as a dentifrice/mouthwash. Patent Document 4, however, does not consider whether or not the detergent composition allows for antibacterialization of teeth or a principal component thereof, hydroxyapatite.

Additionally, if such a high performance antibacterial agent composition and antiviral agent composition can be firmly adhered to a surface of the article, it is also predicted to result in more valuable composition.

Therefore, the present invention has been made to solve the above-discussed problems. An object of the present invention is to provide an antibacterial agent composition which is highly safe and has excellent antibacterial abilities, by using a silicon-containing compound that is obtained by a specific manufacturing method, the antibacterial agent composition having a more stable antibacterial component, being capable of imparting antibacterial abilities to teeth, while being also capable of cleaning an article and the mouth, as well as an antiviral agent composition that ensures both high safety and excellent virus inactivation abilities, and to provide an antibacterializing method and a cleaning/mouth rinsing method, as well as a method for fixing an antibacterial agent and an antiviral agent, each using these compositions.

Means for Solving the Problem

As a result of intensive studies to address the above-mentioned problems, the inventors found an antibacterial agent composition that contains a silicon-containing compound obtained as an antibacterial component by a specific manufacturing method, and an antiviral agent composition that contains a particular silicon-containing compound. Based on this, the present invention is completed.

That is, an antibacterial agent composition of the present invention comprises the composition comprising silicon-containing compound obtained from general formula (a):

$$X-(CH_2)_3-Si-(OCH_2CH_3)_3 \quad (a),$$

wherein X represents halogen ion or organic carbonyloxy ion (organic carboxylate ion), which represents triethoxysilyl compound reacted in ethanol solvent to prepare by general formula (1):

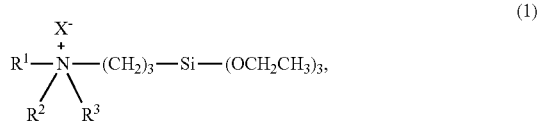

wherein $R^1$ represents an alkyl group having from 12 to 24 carbon atoms; $R^2$ and $R^3$ represent lower alkyl groups, respectively, having from 1 to 6 carbon atoms, which carbon atoms may be the same or different from each other; and X represents a halogen ion or an organic carbonyloxy ion (organic carboxylate ion).

It is desirable that the silicon-containing compound represented by the general formula (1) is octadecyldimethyl(3-triethoxysilylpropyl)ammonium chloride.

The above-mentioned antibacterial agent composition may further contain ethanol, water and even an amphoteric surfactant and/or a cationic surfactant.

An antibacterializing method of the present invention may antibacterialize a surface of an article with the above-described antibacterial agent composition.

A cleaning/mouth rinsing method of the present invention may perform cleaning and mouth rinsing by using the antibacterial agent composition.

An antiviral agent composition of the present invention may comprise a silicon-containing compound represented by general formula (1):

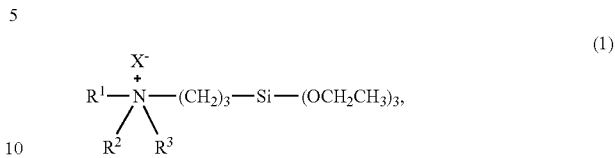

wherein $R^1$ represents an alkyl group having from 12 to 24 carbon atoms; $R^2$ and $R^3$ represent lower alkyl groups, respectively, having from 1 to 6 carbon atoms, which carbon atoms may be the same or different from each other; and X represents a halogen ion or an organic carbonyloxy ion (organic carboxylate ion).

It is desirable that the silicon-containing compound presented by the general formula (1) is octadecyldimethyl(3-triethoxysilylpropyl)ammonium chloride.

The above-mentioned antiviral agent composition may further contain ethanol, water and even an amphoteric surfactant and/or a cationic surfactant.

It is desirable that the antiviral agent composition has the ability to inactivate at least one type of virus selected from the group consisting of type A influenza virus (human, avian, swine (atypical)), type B influenza virus, parainfluenza virus and norovirus.

A method for fixing an antibacterial agent of the present invention may comprise: by means of a article having an oxygen-containing functional group on its surface, applying or spraying the above-described antibacterial agent composition onto the surface of the article, or immersing the article in the antibacterial agent composition.

A method for fixing an antiviral agent of the present invention may comprise using a article having an oxygen-containing functional group on its surface and applying or spraying the antiviral agent composition onto a surface of the article; or immersing the article in the antibacterial agent composition.

Effect of the Invention

With the antibacterial agent composition and the antiviral agent composition of the present invention, since they contain a silicon-containing compound formed by a so-called ethoxy body and having an ethoxy group obtained by a specific manufacturing method, highly toxic methanol is not involved at all during production, transportation or use, and extremely high safety may be ensured as compared with conventional agents containing a silicon-containing compound formed by a methoxy body, while providing excellent antibacterial and antivirus abilities.

In general, bacteria and viruses can take only one or two hours to proliferate until approximately doubled in number. Accordingly, if the number of bacteria and viruses can be reduced 1000 times smaller, then a period of time of tens of hours will be left before they can proliferate to the above-mentioned number. This should provide considerable antibacterial and antivirus abilities. Here, the antibacterial and antivirus abilities achieved by the antibacterial agent composition and the antiviral agent composition of the present invention are such that the number of survival bacteria or the amount of survival viruses can be reduced by several orders of magnitude to substantially zero, as compared with applying conventional agents containing a silicon-containing compound formed by a methoxy body. This makes an extraordinary epoch-making effect and proves very valuable. Such an antiviral ability is very effective against, in particular, type A influenza virus (human, avian, swine (atypical)), type B influenza virus, parainfluenza virus or norovirus.

In addition, a combination of a surfactant specific to the above-described antibacterial agent composition and antiviral agent composition with a particular solvent may ensure stabilization of the antibacterial component for a long period of time, achieve stronger antibacterial abilities and the persistence than would be provided conventionally, and further disinfection/sterilization of a article as well as effective antibacterialization of teeth by mouth rinsing, thereby realizing simple and effective antibacterialization of the teeth or hydroxyapatite.

Moreover, according to the methods for fixing an antibacterial agent and fixing an antiviral agent of the present invention, it is possible to make an antibacterial agent and an antiviral agent adhered to a surface of an article effectively. This allows these agents to fully exploit their own antibacterial and antiviral abilities under high safety conditions.

BEST MODE FOR CARRYING OUT THE INVENTION

Figure 1:
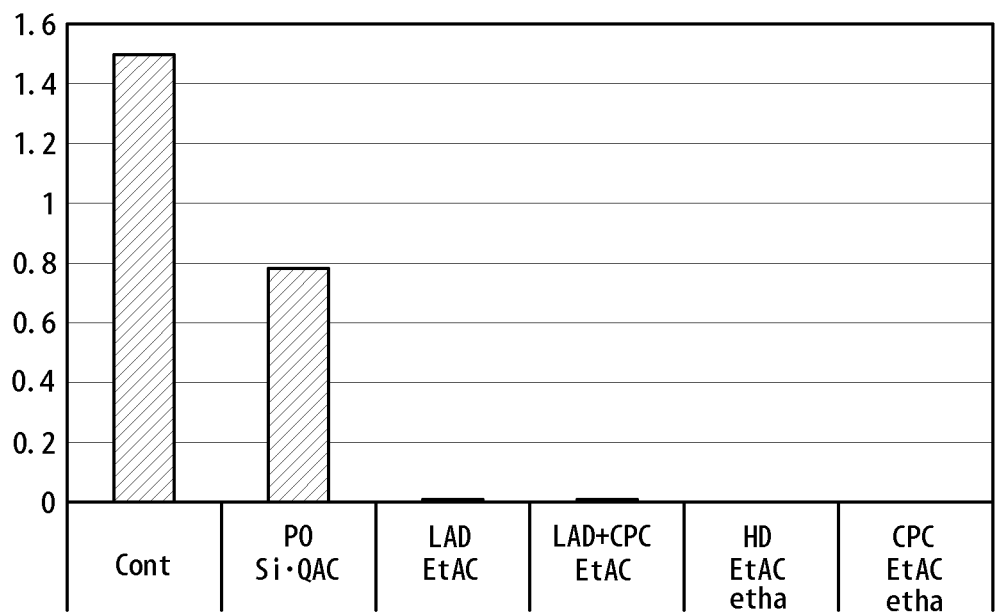
FIG. 1 is a graph depicting the result of a test for comparing antibacterial abilities between EtAC and Si-QAC in Example 3, where the vertical axis represents absorbance.

The present invention will now be described further in detail below.

It should be noted that the term "antibacterial" as used herein means sterilization or impairment of bacteria and eumycetes, or otherwise prevention of their proliferation; and "antiviral" refers to inactivation of pathogenic viruses.

An antibacterial agent composition of the present invention comprises the composition comprising silicon-containing compound obtained from general formula (a):

wherein X represents halogen ion or organic carbonyloxy ion (organic carboxylate ion), which represents triethoxysilyl compound reacted in ethanol solvent to obtain an antibacterial agent composition of the present invention represented by general formula (1):

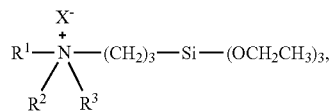

wherein $R^1$ represents an alkyl group having from 12 to 24 carbon atoms; $R^2$ and $R^3$ represent lower alkyl groups, respectively, having from 1 to 6 carbon atoms, which carbon atoms may be the same or different from each other; and X represents a halogen ion or an organic carbonyloxy ion (organic carboxylate ion).

In formulas (a) and (1), X may exemplify a halogen ion, such as chloride ion or bromine ion, and an organic carbonyloxy ion (organic carboxylate ion), such as methylcarbonyloxy ion (acetate ion), ethylcarbonyloxy ion (propionate ion) or phenylcarbonyloxy ion (benzoate ion).

The alkyl group having 12-24 carbon atoms of R1 in the formula (1) may exemplify a dodecyl group, tridecyl group, tetradecyl group, pentadecyl group, hexadecyl group, heptadecyl group, octadecyl group, nonadecyl group, eicosyl group, uneicosyl group, doeicosyl group, trieicosyl group, tetraeicosyl group and so on.

In the formula (1), the lower alkyl groups of 1-6 carbon atoms of R2 and R3 that may be the same or different, may include, for example, a methyl group, ethyl group, propyl group, isopropyl group, butyl group, pentyl group, hexyl group and cyclohexyl group.

That is, the silicon-containing compound represented by the general formula (1) that is contained in the antibacterial agent composition of the present invention is a particular silicon-containing compound obtained by reacting a particular triethoxysilyl compound represented by the general formula (a) in an ethanol solvent. Such a silicon-containing compound represents a so-called ethoxy body of a silicon-containing compound that is bound three ethoxy groups to a silicon atom.

As is the case with conventional silicon-containing compounds, any so-called methoxy body of silicon-containing compound with binding between a methoxy group to a silicon atom and requires methanol during production, and so methanol can be generated by a side reaction, such as hydrolysis, even after production. However, it has been pointed out that methanol is more likely toxic by oral administration, could cause strong eye irritation and have adverse effects on fertility or embryos, cause disorders of central nervous system, visual organ, systemic toxicity or stimulation to respiratory organs, and could also induce sleepiness or dizziness, thereby causing disorders of central nervous system or visual organ due to a long-term or repetitive exposure. Thus, conventionally, the presence of such methanol has endangered the safety of the resultant silicon-containing compound itself, as well as the safety of antibacterial agent compositions containing the compound.

In contrast, according to the present invention, an ethanol solvent is utilized during production of the above-mentioned silicon-containing compound, whereas a highly toxic solvent, such as methanol, is not used at all and no methanol is generated from such a silicon-containing compound formed by an ethoxy body whatsoever by a side reaction, such as hydrolysis. Accordingly, the resultant antibacterial agent composition is extremely safe. Moreover, there is no concern that a silicon-containing compound, such as a methoxy body, is obtained as a by-product when a particular triethoxysilyl compound represented by the general formula (a) is reacted in an ethanol solvent.

Specific examples of the silicon-containing compound represented by the general formula (1) include octadecyldimethyl(3-triethoxysilylpropyl)ammonium chloride, dodecyldimethyl(3-triethoxysilylpropyl)ammonium chloride, dodecyldiisopropyl(3-triethoxysilylpropyl)ammonium chloride, tetradecyldimethyl(3-triethoxysilylpropyl)ammonium chloride, tetradecyldiethyl(3-triethoxysilylpropyl)ammonium chloride, tetradecyldi-n-propyl(3-triethoxysilylpropyl)ammonium chloride, pentadecyldimethyl(3-triethoxysilylpropyl)ammonium chloride, pentadecyldiethyl(3-triethoxysilylpropyl)ammonium chloride, pentadecyldi-n-propyl(3-triethoxysilylpropyl)ammonium chloride, hexadecyldimethyl(3-triethoxysilylpropyl)ammonium chloride, hexadecyldiethyl(3-triethoxysilylpropyl)ammonium chloride, hexadecyldi-n-propyl(3-triethoxysilylpropyl)ammonium chloride, octadecyldiethyl(3-triethoxysilylpropyl)ammonium chloride, octadecyldi-n-propyl(3-triethoxysilylpropyl)ammonium chloride, and so on. Among these, octadecyldimethyl(3-triethoxysilylpropyl)ammonium chloride is preferable for the least biological toxicity, the least environmental load during use and the least environmental load of wastewater.

To produce the above-described silicon-containing compound, a particular triethoxysilyl compound represented by the general formula (a) is reacted in an ethanol solvent. By reacting these in an ethanol solvent, generation of by-products such as methoxy bodies can be effectively suppressed and the safety of the resultant silicon-containing compound can be significantly improved. Specifically, a particular triethoxysilyl compound represented by the general formula (a) is reacted in an ethanol solvent with an amine represented by general formula (b):

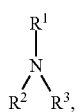

(b)

wherein $R^1$ represents an alkyl group having from 12 to 24 carbon atoms; $R^2$ and $R^3$ represent lower alkyl groups, respectively, having from 1 to 6 carbon atoms, which carbon atoms may be the same or different from each other.

More specifically, for example, if octadecyldimethyl(3-triethoxysilylpropyl) ammonium chloride is produced, triethoxysilylpropyl chloride, as a triethoxysilyl compound represented by the general formula (a), N,N-dimethyloctadecylamine, as an amine represented by the general formula (b), and ethanol are fed into a reactor, heated typically to 100-180° C., preferably to 120-150° C., and then reacted typically for 10-60 hours, preferably for 20-40 hours. It is desirable that the mole ratio of triethoxysilyl compound to amine for reaction is normally 1.5:0.8-1:1. It should be noted that the concentrations of the triethoxysilyl compound and amine in ethanol may be changed as necessary without limitation.

Although not limited to a particular value as long as the antibacterial effect and the persistence are ensured, the content of the above-described silicon-containing compound in the antibacterial agent composition of the present invention is normally 0.6 ppm or more, preferably 20 ppm or more, more preferably 0.006-24% by weight, and most preferably 0.06-6% by weight. The silicon-containing compound is preferably within the aforementioned ranges for obtaining a sufficient antibacterial effect and the persistence.

The antibacterial agent composition of the present invention may further contain ethanol. Without limitation, the content of ethanol is preferably 50-85% by volume with respect to the fixing on antibacterial effect. In addition, the content of ethanol is preferably 35-85% by volume with respect to fixing such an antibacterial agent composition to a article. The antibacterial agent composition may further contain water. That is, the antibacterial agent composition may contain, as a solvent, either water, ethanol or an ethanol aqueous solution (such solvent will be referred to hereinafter as "water and/or ethanol"). When any of the above is used as a solvent, as long as the content of the above-described silicon-containing compound falls within the above-mentioned range, each of these solvents has an extremely low toxicity in comparison to methanol, and may significantly improve the safety of the resultant antibacterial agent composition. This may provide an agent that combines high safety with excellent antibacterial effect.

Moreover, such an antibacterial agent composition may contain, depending on the usage, at least one type of amphoteric surfactant or at least one type of cationic surfactant or both amphoteric and cationic surfactants. Among these, it is desirable to contain the amphoteric surfactant. If these surfactants are contained, it becomes easier to make the silicon-containing compound stable in an agent, thereby preventing cloudiness and gelation of the solution.

The above-described amphoteric surfactant is preferably of at least one type selected from the group consisting of betaine-based and amine oxide-based surfactants. Among these, an amine oxide-based amphoteric surfactant is preferable in favor of further stabilization of antibacterial component.

Examples of the betaine-based amphoteric surfactant include coco fatty acid amidepropyl carboxybetaine, betaine lauryldimethyl aminoacetate, imidazolium betaine and so on. Among these, coco fatty acid amidepropyl carboxybetaine and betaine lauryldimethyl aminoacetate are preferable in favor of stability of the silicon-containing compound which is an antibacterial component in water and/or ethanol.

Examples of the amine oxide-based amphoteric surfactant include lauryl dimethyl amine oxide, lauroylamidopropyl dimethylamine oxide and so on. Among these, lauryl dimethyl amine oxide is preferable in favor of long-term stability of the silicon-containing compound which is an antibacterial component in water and/or ethanol.

Examples of the cationic surfactant include: a cationic surfactant (except the silicon-containing compound), such as cetylpyridinium chloride; N-cocoyl-alginine ethyl ester pyridone carboxylate; and so on represented by general formula (2):

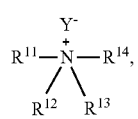

(2)

wherein $R^{11}$ represents a hydrocarbon group having 6 or more carbon atoms; $R^{12}$, $R^{13}$ and $R^{14}$ represent lower hydrocarbon groups, respectively, which hydrocarbon groups may be the same or different from each other; Y represents a halogen ion or an organic carbonyloxy ion.

In the cationic surfactant presented by the general formula (2), it is preferred that $R^{11}$ represents an alkyl group having 10 to 25 carbon atoms, R12, $R^{13}$ and $R^{14}$ are lower alkyl groups having 1 to 6 carbon atoms that may be the same or different, and Y represents a halogen ion or an organic carbonyloxy ion (organic carboxylate ion).

Examples of the hydrocarbon group R11 having 6 or more carbon atoms of the cationic surfactant represented by the general formula (2) may include hexyl group, heptyl group, octyl group, nonyl group, decyl group, decyl group, dodecyl group, tridecyl group, tetradecyl group, pentadecyl group, hexadecyl group, heptadecyl group, octadecyl group, nonadecyl group, eicosyl group, uneicosyl group, doeicosyl group, trieicosyl group, tetraeicosyl group, pentaeicosyl group and so on.

Examples of R12, R13 and R14 of the cationic surfactant represented by the general formula (2) may include methyl group, ethyl group, propyl group, isopropyl group, butyl group, pentyl group, hexyl group, cyclohexyl group, phenyl group, tolyl group and so on.

Specific examples of the cationic surfactant represented by the general formula (2) may include the following compounds: decyltrimethylammonium chloride, decyltriethylammonium acetate, dodecyltrimethylammonium acetate, dodecyltriisopropylammonium bromide, tridecyltriethylammonium bromide, tetradecyltrimethylammonium chloride, tetradecyltriethylammonium chloride, tetradecyltri-n-propylammonium chloride, pentadecyltrimethylammonium chloride, pentadecyltriethylammonium chloride, pentadecyltri-n-propylammonium chloride, hexadecyltrimethylammonium chloride, hexadecyltriethylammonium chloride, hexadecyltri-n-propylammonium chloride, octadecyltrimethylammonium chloride, octadecyltriethylammonium chloride, octadecyltri-n-propylammonium chloride and so on. Among these, hexadecyltrimethylammonium is most preferable.

Among the above-listed cationic surfactants, hexadecyltrimethylammonium and cetylpyridinium chloride are particularly preferable since they may further improve the antibacterial ability and stability.

In addition, particularly, when a low content of the silicon-containing compound is used under a short term treatment condition, among the above-listed amphoteric and cationic surfactants, lauryl dimethyl amine oxide which is a amphoteric surfactant is particularly preferable with respect to better antibacterial abilities. It is estimated that the reason why a remarkable antibacterial ability is obtained even under a severe condition is that an intermediate is produced by the reaction of lauryl dimethyl amine oxide with the silicon-containing compound, and such an intermediate contributes to enhancement of reactivity as an antibacterial component.

The content of the amphoteric surfactant is normally 0.007-20 w/v %, preferably 0.05-10 w/v %. The amphoteric surfactant is preferably within the aforementioned ranges in order to obtain a sufficient antibacterial effect and the persistence. Particularly, when the silicon-containing compound in the above-described antibacterial agent composition is fixed to an article, such as a dental material, a textile product including a towel or clothes, the silicon-containing compound in the antibacterial agent composition may demonstrate its effect to a sufficient extent if the content of the silicon-containing compound is normally not less than 0.03% by weight, preferably not less than 0.06% by weight. It is desirable, without limitation, that the upper limit is equal to or less than 0.6% by weight, in terms of cost. Further, if a cationic surfactant is contained, the content of the cationic surfactant is preferably 0.01-5 w/v %, and preferably 0.05-1 w/v % with respect to improvement of the stability and antibacterial ability of the silicon-containing compound.

The antibacterial agent composition may also be used as a detergent composition for exerting a detergent effect, in particular, if containing a amphoteric surfactant. Such a detergent composition may remain stable for a long period of time without cloudy gelation of the silicon-containing compound which is an antibacterial agent composition thereof, offer stronger antibacterial abilities than the conventional detergent compositions, and further enable antibacterialization of teeth. Accordingly, it is useful as a dentifrice/mouthwash for treatment/prevention of dental caries, periodontal diseases and other dental infectious diseases, aspiration pneumonia and so on. In addition, such a detergent composition may further contain at least one type of cationic surfactant. The antibacterial ability, antibacterial persistence and stability of the detergent composition of the present invention may be further improved by addition of the cationic surfactant.

The antibacterial agent composition is also useful, especially when containing a cationic surfactant, as a composition for disinfection, cleaning, mouth rinsing, sterilization and antibacterialization for disinfecting, cleaning, sterilizing and antibacterializing composition. Such a composition for disinfection, cleaning, mouth rinsing, sterilization and antibacterialization may be used as a dentifrice/mouthwash for treatment/prevention of dental caries, periodontal diseases and other dental infectious diseases, aspiration pneumonia and so on since it allows for antibacterialization of teeth as is the case with the antibacterial agent composition of the present invention.

The content of the silicon-containing compound in these detergent composition and composition for disinfection, cleaning, mouth rinsing, sterilization and antibacterialization is normally 0.6 ppm or more, preferably 20 ppm or more, more preferably from 0.006 to 24% by weight, and most preferably from 0.06 to 6% by weight, as is the case with the antibacterial agent composition of the present invention as mentioned earlier. The silicon-containing compound is preferably within the aforementioned ranges for obtaining a sufficient antibacterial ability and the persistence. Particularly, when the silicon-containing compound in the above-described composition for sterilization, cleaning, mouth cleaning, sterilization and antibacterialization is fixed to an article, such as a dental material, a textile product including a towel or clothes, the silicon-containing compound in that composition may sufficiently demonstrate its effect if the content of the silicon-containing compound is normally not less than 0.03% by weight, preferably not less than 0.06% by weight. It is desirable, without limitation, that the upper limit is equal to or less than 0.6% by weight, in terms of cost.

The content of cationic surfactant in the above-described composition for disinfecting, cleaning, sterilization and antibacterialization is preferably from 0.01 to 5 w/v %, and preferably from 0.5 to 3 w/v %, with respect to improving the stability and antibacterial ability of the above-described silicon-containing compound in water and/or ethanol.

The antibacterializing method of the present invention may exert disinfection, cleaning, sterilization and antibacterialization effects, and characterized by disinfection/cleaning/sterilization/antibacterialization of a surface of the article with the antibacterial agent composition (detergent composition) of the present invention. Specifically, the disinfection/cleaning/sterilization/antibacterialization of the article with the antibacterial agent composition may be performed by immersing the article in the antibacterial agent composition; applying or spraying the above-described antibacterial agent composition onto a surface of the article; rinsing a surface of the article several times with the antibacterial agent composition; or wiping a surface of the article with a cloth or the like soaked with the antibacterial agent composition. Accordingly, any methods can be used without limitation that allow for contact between the article and the antibacterial agent composition for a predetermined period of time. In addition, a predetermined period of time can be the time to sufficiently react the antibacterial component comprising the above antibacterial agent composition with the surface of an article, and may be selected appropriately. It should be noted that following the disinfection/cleaning/sterilization/antibacterialization with the antibacterial agent composition, the antibacterial agent composition may be eliminated from the surface of an article by washing with water, if necessary.

Articles to be disinfected/cleaned/sterilized/antibacterialization by the antibacterializing method of the present invention may include various articles, including dental materials such as implants, crowns, bridges, orthodontic brackets or dental wires, and other articles such as tableware, glasses, sinks, kitchen goods, toilet bowls, toilet goods, bathtubs, bath goods, lavatory bowls, lavatory goods, textile products including towels or clothes, and so on.

In addition, the cleaning/mouth rinsing method of the present invention may sterilize and antibacterialize the article, wherein the method is characterized by disinfection/cleaning/sterilization/antibacterialization with the antibacterial agent composition of the present invention (the composition for disinfection, cleaning, mouth rinsing, sterilization and antibacterialization). Specifically, this may be performed by immersing the article in the antibacterial agent composition, wiping a surface of the article with a cloth or the like soaked with the antibacterial agent composition, or applying or spraying the antibacterial agent composition onto the article. Accordingly, any method can be used without limitation that allow for contact between the article and the antibacterial agent composition for a predetermined period of time. In addition, a predetermined period of time can be the time to sufficiently react the antibacterial component comprising the above antibacterial agent composition with the surface of an article, and may be selected appropriately. Alternatively, the antibacterial agent composition of the present invention (the composition for disinfection/cleaning/mouth rinsing/sterilization/antibacterialization) may also be used for mouth rinsing. Specifically, mouth rinsing with the antibacterial agent composition may be performed, e.g., by rinsing the oral cavity through gargling with the antibacterial agent composition for mouth rinsing.

According to this cleaning/mouth rinsing method, the above-described antibacterial agent composition offering an excellent antibacterial ability imparting performance and a persistent antibacterial property may be used to clean/disinfect/sterilize the mouth effectively and impart excellent antibacterial abilities and persistent antibacterial properties to teeth.

In the method for stabilizing said silicon-containing compound in water and/or ethanol, moreover, a method for stabilizing the silicon-containing compound of the present invention represented by the general formula (1) in water and/or ethanol may also be adopted based on the use of at least one type of amine oxide-based amphoteric surfactant. The silicon-containing compound represented by the general formula (1) may coexist with an amine oxide-based amphoteric surfactant in water and/or ethanol, which results in said silicon-containing compound being stabilized in water and/or ethanol over a long period of time. As a result, an antibacterial agent composition may be produced that prevents cloudiness and gelation of the solution and offers excellent antibacterial abilities and persistent antibacterial properties.

In the method for stabilizing the silicon-containing compound of the present invention represented by the general formula (1) in water and/or ethanol, at least one type of amine oxide-based amphoteric surfactant may also be used together with at least one type of cationic surfactant, in which case similar results can be obtained.

In the method for stabilizing the silicon-containing compound of the present invention represented by the general formula (1) in water and/or ethanol, the silicon-containing compound represented by the general formula (1), the amine oxide-based amphoteric surfactant and the cationic surfactant are the same as those contained in the antibacterial agent composition of the present invention. In addition, it is preferred that the contents of the silicon-containing compound and the amine oxide-based amphoteric surfactant are within the same range as those contained in the antibacterial agent composition of the present invention for the silicon-containing compound to be stabilized in water and/or ethanol and the resultant solution to exert an antibacterial effect and the persistence in a sufficient manner. It should be noted that if a cationic surfactant is used, the content of the cationic surfactant is preferably within the same range as that contained in the antibacterial agent composition with respect to improve stability and antibacterial ability of the silicon-containing compound.

In addition, the method for stabilizing the silicon-containing compound of the present invention represented by the general formula (1) in water and/or ethanol uses at least one type of cationic surfactant in a method for stabilizing the silicon-containing compound in water and/or ethanol. The silicon-containing compound represented by the general formula (1) may coexist with the cationic surfactant in water and/or ethanol, which results in said silicon-containing compound being stabilized in water and/or ethanol over a long period of time. As a result, an antibacterial agent composition may be produced that prevents cloudiness and gelation of the solution, offers excellent antibacterial abilities and persistent antibacterial properties, and achieves disinfection and sterilization.

In the method for stabilizing the silicon-containing compound of the present invention represented by the general formula (1) in water and/or ethanol, the silicon-containing compound represented by the general formula (1) and the cationic surfactant are the same as those contained in the antibacterial agent composition of the present invention. In addition, it is preferred that the contents of the silicon-containing compound and the cationic surfactant are within the same range as those contained in the antibacterial agent composition of the present invention for the silicon-containing compound to be stabilized in water and/or ethanol and the resultant solution to exert an antibacterial effect and the persistence in a sufficient manner.

In addition, the antibacterial agent composition of the present invention may also antibacterialize teeth or hydroxyapatite. The antibacterial agent composition of the present invention may simply provide teeth or hydroxyapatite which is a principal component of the teeth with an excellent antibacterial ability such that the ability lasts for a long period of time. It is preferred that antibacterialization is performed with the antibacterial agent composition of the present invention since an excellent antibacterial ability can last for a longer period of time.

The antibacterialization of the teeth or hydroxyapatite with antibacterial agent composition of the present invention may be performed by, specifically, immersing the teeth or hydroxyapatite in the antibacterial agent composition of the present invention, applying or spraying the antibacterial agent composition of the present invention onto a surface of the teeth or hydroxyapatite, or wiping the surface of the teeth or hydroxyapatite with a cloth or the like soaked with the antibacterial agent composition of the present invention. Accordingly, any methods can be used without limitation that allows contact between the teeth or hydroxyapatite and the antibacterial agent composition for a predetermined period of time. In addition, a predetermined period of time can be the time to sufficiently react the antibacterial component comprising the above antibacterial agent composition onto the surface of an article, and may be selected appropriately.

An antiviral agent composition of the present invention may comprise a silicon-containing compound represented by the general formula (1):

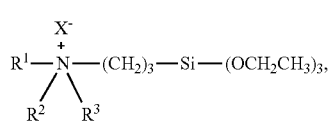

wherein $R^1$ represents an alkyl group having from 12 to 24 carbon atoms; $R^2$ and $R^3$ represent lower alkyl groups, respectively, having from 1 to 6 carbon atoms, which carbon atoms may be the same or different from each other; and X represents a halogen ion or an organic carbonyloxy ion (organic carboxylate ion). In the general formula (1), $R^1$, $R^2$, $R^3$ and X are defined to have the same meaning as those of the silicon-containing compound in the above-mentioned antibacterial agent composition of the present invention. No highly toxic methanol is produced by a side reaction, such as hydrolysis, from such a silicon-containing compound formed by an ethoxy body, which compound is thus very safe. If such a compound is contained, such an antiviral agent composition that has both high safety and excellent antiviral ability can be achieved.

Specific examples of the silicon-containing compound represented by the general formula (1) include octadecyldimethyl(3-triethoxysilylpropyl)ammonium chloride, dodecyldimethyl(3-triethoxysilylpropyl)ammonium chloride, dodecyldiisopropyl(3-triethoxysilylpropyl)ammonium chloride, tetradecyldimethyl(3-triethoxysilylpropyl)ammonium chloride, tetradecyldiethyl(3-triethoxysilylpropyl)ammonium chloride, tetradecyldi-n-propyl(3-triethoxysilylpropyl)ammonium chloride, pentadecyldimethyl(3-triethoxysilylpropyl)ammonium chloride, pentadecyldiethyl(3-triethoxysilylpropyl)ammonium chloride, pentadecyldi-n-propyl(3-triethoxysilylpropyl)ammonium chloride, hexadecyldimethyl(3-triethoxysilylpropyl)ammonium chloride, hexadecyldiethyl(3-triethoxysilylpropyl)ammonium chloride, hexadecyldi-n-propyl(3-triethoxysilylpropyl)ammonium chloride, octadecyldiethyl(3-triethoxysilylpropyl)ammonium chloride, octadecyldi-n-propyl(3-triethoxysilylpropyl)ammonium chloride and so on. Among these, octadecyldimethyl(3-triethoxysilylpropyl)ammonium chloride is preferable for the least biological toxicity, the least environmental load during use and the least environmental load of wastewater.

Preferably, the silicon-containing compound represented by the general formula (1) is obtained by reacting the triethoxysilyl compound represented by the general formula (a) in an ethanol solvent:

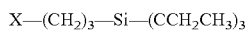 (a), wherein X represents a halogen ion or an organic carbonyloxy ion (organic carboxylate ion). Such a triethoxysilyl compound is the same as the triethoxysilyl compound in the antibacterial agent composition of the present invention, and is produced by the same method as the silicon-containing compound in the antibacterial agent composition of the present invention. That is, such a reaction eliminates the need for using a highly toxic solvent, such as methanol, even when producing the above-described silicon-containing compound, which may result in a safer antiviral agent composition.

In addition, although not limited to a particular value as long as the antiviral effect and the persistence are ensured, the content of the above-described silicon-containing compound in the antiviral agent composition of the present invention is normally 0.6 ppm or more, preferably 20 ppm or more, more preferably from 0.006 to 24% by weight, and most preferably from 0.06 to 6% by weight. The silicon-containing compound is preferably within the aforementioned ranges for obtaining a sufficient antiviral effect and the persistence.

The antiviral agent composition of the present invention may further contain ethanol. Without limitation, the content of ethanol is preferably 50-85% by volume with respect to fixing primarily on antiviral effect. In addition, the content of ethanol is preferably 35-85% by volume in favor of fixing such an antiviral agent composition to a substance. The antiviral agent composition may further contain water. That is, the antiviral agent composition may contain, as a solvent, any of water, ethanol or an ethanol aqueous solution (water and/or ethanol). Any of these solvents has an extremely low toxicity in comparison to methanol and may significantly improve the safety of the resultant antiviral agent composition. This may provide an agent that combines high safety with excellent antiviral effect. In this way, by only comprising the silicon-containing compound, and, if necessary, water and/or ethanol, pathogenic viruses may be inactivated in a simple and effective manner and infection spread of pathogenic viruses may be prevented, thereby enhancing the hygiene environment.

Examples of viruses that can be inactivated by the antiviral agent composition include type A influenza virus (humans, avian, swine (atypical)), type B influenza virus, parainfluenza virus, (type A-E) hepatitis virus, measles virus, herpes virus, mumps virus, enveloped virus, such as rabies virus or influenza virus, norovirus, HIV virus and so on. Among these, influenza virus and norovirus are preferable, and in particular, this antiviral agent composition proves highly valuable, in particular, with respect to the fact that it exerts an excellent inactivation ability against type A influenza virus (swine (atypical)) (atypical (swine) influenza virus (type H1N1)).

Moreover, such an antiviral agent composition may contain, depending on the usage, at least one type of amphoteric surfactant or at least one type of cationic surfactant or both amphoteric and cationic surfactants. Above all, it is desirable to contain the amphoteric surfactant. If these surfactants are contained, it becomes easier to make the silicon-containing compound stable in an agent, thereby preventing cloudiness and gelation of the solution. It should be noted that the available types and contents of the amphoteric surfactant and the cationic surfactant are the same as those described in relation to the above antibacterial agent composition of the present invention.

The inactivation of viruses with the antiviral agent composition of the present invention may be specifically performed by immersing the article to which viruses may be attached in the antiviral agent composition; applying or spraying the antiviral agent composition onto the article; or wiping a surface of the article with a cloth or the like soaked with the antiviral agent composition. Accordingly, any methods can be used without limitation that allow for contact between the article and the antiviral agent composition for a predetermined period of time. In addition, a predetermined period of time can be the time to sufficiently react the antibacterial component comprising the above antibacterial agent composition onto a surface of the article, and may be selected appropriately.

The method for fixing the antibacterial agent of the present invention characterized by applying or spraying the antibacterial agent composition onto a surface of the article; or immersing the article in the antibacterial agent composition, by utilizing the substance comprising oxygen functional group on its surface. Similarly, the method for fixing the antiviral agent of the present invention characterized by applying or spraying the antibacterial agent composition onto a surface of the article; or immersing the article in the antibacterial agent composition, by utilizing an article comprising oxygen functional group on its surface. That is, these methods for fixing the antibacterial agent and for fixing the antiviral agent correspond to a method for applying or spraying the antibacterial agent composition or the antiviral agent composition onto a surface, or a method for immersing the article in the antibacterial agent composition or the antiviral agent composition, in each case a substance having an oxygen-containing functional group, such as an —OH or —O— group, on its surface is used. As described above, since the antibacterial agent composition or the antiviral agent composition contain the silicon-containing compound having an ethoxy group represented by the general formula (1), such an ethoxy group reacts with an oxygen-containing functional group on the surface of the treated article to release ethanol, while being linked together by covalent bonding via oxygen. As a result, an antibacterial or antiviral active site of the silicon-containing compound is firmly fixed to the surface of the treated article, and a strong antibacterial or antiviral ability and an excellent persistence are imparted to the surface of the treated article.

The treated article may be any substance that has an oxygen-containing functional group, such as —OH or —O— group on its surface, including, but not limited to, ranging from minute articles, such as dental materials, to other articles, such as textile products including towels or clothes, and further to large articles. In addition, to apply such an oxygen-containing functional group to a surface of the article, surface treatment may be performed in advance to apply the oxygen-containing functional group to the surface of the treated article prior to application of the antibacterial or antiviral agent composition. Such surface treatment is preferably, for example, ozone water treatment, and more specifically, includes treatments for immersing in ozone water, spraying ozone water or applying ozone water. Since such ozone water treatment specifically involves a simple process including immersion, spraying, application by means of ozone water, this allows for flexible support of any articles, for example, from minute articles to large articles, and easy treatment and incorporation in a production line. Thus the antibacterial or antiviral agent composition can be fixed to a surface of an article more firmly.

The above-described process with ozone water may be performed, without limitation, for example, by using ozone water with appropriately adjusted concentration, while changing the treatment times depending on the concentration of that ozone water as necessarily. Specifically, for example, if the concentration of ozone is from 0.4 to 0.6 ppm, then immersion treatment only may be performed for about 5 minutes; and for normal ozone water in a concentration of several ppm, only simple spray and natural dry treatment has to be performed to provide the article with a more sufficient antibacterial ability or antiviral ability and the persistence.

EXAMPLE

While examples of the present invention will be presented specifically, the present invention is not limited to the disclosed examples. Meanwhile, the following abbreviations are used in the examples:
 EtAC: octadecyldimethyl(3-triethoxysilylpropyl)ammonium chloride
 Si-QAC: octadecyldimethyl(3-trimethoxysilylpropyl)ammonium chloride
 CPB: cetylpyridinium bromide
 Aromox®: lauryl dimethyl amine oxide (manufactured by Lion Corporation)
 LAD: lauroyl amidepropyl dimethyl amine oxide (manufactured by Kawaken Fine Chemicals Co., Ltd.)
 HD: hexadecyltrimethylammonium chloride
 CPC: cetylpyridinium chloride
 PO: polyoxyethylene sorbitan monolaurate
 CDE: coco fatty acid diethanolamide
 ethanol for disinfection (70%): (alcohol for disinfection of as defined by the Japanese Pharmacopoeia)

Synthesis Example 1

Synthesis of Dimethyloctadecyl[3-(triethoxysilyl) propyl]Ammonium Chloride Ethanol Solution Firstly, 41.5 g (0.17 moL) of triethoxysilylpropyl chloride (Tokyo Kasei Kogyo Co., Ltd.), 44.6 g (0.150 moL) of N,N-dimethyl octadecylamine (Tokyo Kasei Kogyo Co., Ltd.) and 40.5 g of ethanol are fed into a nitrogen-purged pressurized reactor and heated to 135° C. After the reaction for 20 hours, 121.4 g of dimethyloctadecyl[3-(triethoxysilyl)propyl]ammonium chloride (EtAC) in ethanol solution is obtained.

Content: 63.8% Net Amount: 77.5 g Yield: 95.9%

It should be noted that the identification of dimethyloctadecyl[3-(triethoxysilyl)propyl]ammonium chloride is performed by MS. The measurement conditions and spectral data are as follows:
 1) Measurement Conditions:
 Mass range: 22.0458-711.451 m/z
 Ionization method: FAB (fast atom bombardment)
 Mode: positive
 2) Spectral Data: m/z=530

Safety Test Examples 1-3

To ascertain the safety of the composition of the present invention containing octadecyldimethyl(3-triethoxysilylpropyl)ammonium chloride, a mutagenicity test, an acute oral toxicity test with female mice and a primary skin irritation test with rabbits are conducted.

Test Example 1

Mutagenicity Test

As a specimen, the 60 wt. % EtAC ethanol solution obtained in Synthesis Example 1 (a light yellow transparent liquid) is used, and for the purpose of testing mutagenicity of such a specimen, a reverse mutation assay is performed with four *Escherichia coli* WP2uvrA and *Salmonella typhimurium*

TA series strains (TA100, TA1535, TA98 and TA1537) in accordance with Ministry of Labour Notification No. 77 (Sep. 1, 1988). In this test, a bacterial liquid for assay is obtained by inoculating a defrosted bacteria-dispensed cryopreservation liquid into a baffle conical flask, into which 15 mL of nutrient broth medium [OXOID, Nutrient broth No. 2] is dispensed, which is then subjected to gyratory culture at 37° C. for 10 hours. The specimen is sampled and added injection water, and then a test stock solution is prepared and diluted as appropriate with injection water, after which a test liquid is prepared. As positive control substances, 2-(2-furyl)-3-(5-nitro-2-furyl)acrylamide, sodium azide, 9-Aminoacridine hydrochloride and 2-Aminoanthracene are used. The injection water is considered as negative control, and the test is then performed in a dose of 0.610-1250 µg/plate.

As a result, in a sterility test, neither the test stock solution nor the S9mix exhibit a twofold or greater increase in the number of reverse mutant colonies as compared with the negative control value. In this case, no growth of bacteria is observed. In contrast, 2-(2-furyl)-3-(5-nitro-2-furyl)acrylamide, sodium azide and 9-Aminoacridine hydrochloride used as positive control exhibit a remarkable increase in the number of reverse mutant colonies as compared with negative control. In addition, 2-Aminoanthracene induces an obvious reverse mutation in the presence of S9mix. From this, the mutagenicity of the specimen under the conditions of Test Example 1 is determined as negative.

Test Example 2

Acute Oral Toxicity Test with Female Mice

The 60 wt. % EtAC ethanol solution obtained in Synthesis Example 1 is diluted with an injection solution to prepare 400, 300, 200 and 100 mg/ml of test liquids. This solution is orally administered to mice with a dosage of 8,000, 6,000, 4000 and 2,000 mg/kg, whereas control group is orally administered single dose of water for injection to female mice, which are then observed for 14 days.

As a result, for all samples in the groups administered 8,000, 6,000, 4,000 mg/kg and 2 samples in the group administered 2,000 mg/kg, a decrease in locomotor activity is observed 5 minutes after the administration, but they recover within 4 hours after the administration and no abnormality is recognized thereafter (zero dead sample under all conditions). This shows that the LD50 value obtained by the single oral administration in the specimen mice is 8,000 mg/kg or more.

Test Example 3

Primary Skin Irritation Test with Rabbits

The EtAC ethanol solution obtained in Synthesis Example 1 is diluted with ethanol for disinfection (80% ethanol) to prepare a 80% ethanol solution of 3 wt. % EtAC, which is then sprayed on a 100% cotton towel, left at room temperature for 3 minutes, then washed under running water and dried, by which an EtAC-treated towel is fabricated. Such a treated towel is considered as a specimen, and a primary skin irritation test with rabbits is conducted in accordance with OECD Guidelines for the Testing of Chemicals 404 (2002). The specimen, which is cut to about 2 cm by 3 cm, is wetted with about 0.5 mL of injection water, which is then applied to three rabbits at each single site of a wound skin and an intact skin of each rabbit for 24 hours.

As a result, a very slight erythema (one mark) is seen in the wound skin of one sample after 1 hour of the removal, but it disappears within 24 hours and no irritation response is observed afterwards. In the remaining application sites, no irritation response is observed throughout the observation period. Primary irritation index (P.I.I.), which is required in accordance with Federal Register (1972), is 0.1, and the specimen is assessed as in the category of "Non-irritant" in the primary skin irritation test with rabbits.

Example 1

Stability Test in 3 wt. % EtAC Aqueous Solution

The 60 wt. % EtAC ethanol solution obtained in Synthesis Example 1 is mixed with water and various surfactants and the stability is compared between them. The surfactants used are CPB, Aromox and LAD as amphoteric surfactants, HD and CPC as cationic surfactants, and PO and CDE as non-ionic surfactants. The final concentration of EtAC is adjusted to 3 wt. %. The final concentration of each surfactant is adjusted such that the non-ionic surfactant and the amphoteric surfactant are 1 wt. % and the cationic surfactant 0.1 wt. %. The resultant solutions are observed for the presence of precipitation after form 5 days to 2 weeks. The results are shown in Tables 1-2.

TABLE 1

|   | Surfactant | after 5 days | after 2 weeks onward |
|---|---|---|---|
| 1 | Aromox | clear | clear |
| 2 | LAD | clear | clear |
| 3 | Aromox + CPC | clear | clear |
| 4 | LAD + CPC | clear | clear |
| 5 | none | cloudy | cloudy |
| 6 | PO | clear | cloudy |
| 7 | CDE | clear | cloudy |

TABLE 2

|   | Surfactant | after 5 days |
|---|---|---|
| 8 | CPC | clear |

The solutions using amphoteric surfactant or amphoteric surfactant+cationic surfactant do not form a precipitate even after 2 weeks, and are thus found to be stable (Table 1; Entry 1-4).

In contrast, for comparison purposes, a surfactant-free solution, a non-ionic surfactant and a cationic surfactant are also subjected to a similar test, in which case a precipitate is formed at the time point of passing 5 days to 2 weeks, respectively (Table 1; Entry 5-7).

Example 2

Stability Test in 3 wt. % EtAC Ethanol Solution for Disinfection

The 60 wt. % EtAC ethanol solution obtained in Synthesis Example 1 is mixed with cationic surfactants, which are then diluted twenty-fold with ethanol for disinfection and prepared such that the final concentration of EtAC is 3 wt. % and the final concentration of the surfactant 1 wt. %, respectively. HD and CPC are used as the cationic surfactants. The resultant solutions are verified for the presence of precipitation. The results are shown in Table 3.

TABLE 3

| | Surfactant | |
|---|---|---|
| 1 | none | cloudy |
| 2 | HD | clear |
| 3 | CPC | clear |

The solutions with addition of HD and CPC do not form a precipitate and are thus found to be stable (Table 3; Entry 2 and 3).

In contrast, for comparison purposes, a surfactant-free solution is also subjected to a similar test, in which case precipitate is formed several hours after mixing (Table 3; Entry 1).

Example 3

Test 1 for Comparing Antibacterial Abilities Between EtAC and Si-QAC

A 60 wt. % Si-QAC methanol solution or the 60 wt. % EtAC ethanol solution obtained in Synthesis Example 1 is mixed with a surfactant, which is then diluted twenty-fold with water or ethanol for disinfection, and prepared such that the final concentrations of EtAC or Si-QAC and the surfactant are:

3% SiQAC+1% PO, 3% EtAC+1% LAD, 3% EtAC+1% LAD+0.1% CPC (three specimens of aqueous solution); and 3% EtAC+0.1% HD, 3% EtAC+0.1% CPC (two specimens of ethanol for disinfection solution).

Cover glasses for counting chamber are immersed in MQ water (control) and the five resultant solution specimens for 30 minutes, respectively, which are then removed and left for an hour before washing with water to remove excess solution. Then, 50 µL of bacteria suspension of $10^6$ CFU/mL *Candida albicans* GDH18 is inoculated, left at room temperature for 2 hours, then added 3 mL of Sabouraud medium and cultured at 37° C. for 22 hours.

Absorbance is used for calculation of the number of bacteria (wavelength: 600 nm, measurement device: BioPhotometer). The absorbance of 0.3 is equivalent to $10^7$ CFU/mL.

The results are reported in FIG. 1. As illustrated in FIG. 1, bacterial growth is not observed at all on the glass surface which is treated with 3% EtAC+1% LAD (LADEtAC), 3% EtAC+1% LAD+0.1% CPC (LAD+CPCEtAC), 3% EtAC+ethanol for disinfection solution of 0.1% HD (HDEtAC eth) and 3% EtAC+ethanol for disinfection solution of 0.1% CPC (CPCEtAC eth), whereas Si-QAC (POSi-QAC) involves a bacterial proliferation of about $2.6 \times 10^7$ CFU/mL, suggesting that a very strong antibacterial ability is obtained even compared with conventional silicon-containing compounds of methoxy body.

Example 4

Comparison Test 2 for Antibacterial Abilities Between EtAC and Si-QAC

A 60 wt. % Si-QAC methanol solution or the 60 wt. % EtAC ethanol solution obtained in Synthesis Example 1 is mixed with a surfactant and water, which is then prepared such that the final concentrations of EtAC or Si-QAC and the surfactant are:

3% SiQAC+1% PO, 3% SiQAC+1% PO+HD, 3% SiQAC+1% LAD, 3% EtAC+1% LAD, 3% EtAC+1% LAD+0.1% CPC (aqueous solutions).

Cover glasses for counting chamber are immersed in the resultant solutions for 45 minutes, removed and washed with water to remove excess solution, then left and dried for 1 hour, which is used in an experiment. Subsequently, 50 µL of bacteria suspension of $10^6$ CFU/mL *C. albicans* GDH18 is inoculated, left at room temperature for 2 hours, then added 3 mL of Sabouraud medium is added and cultured at 37° C. for 24, 48 and 90 hours.

For the number of bacteria, a *Candida* yellow medium is used for simple calculation. The color of the medium remains red if bacteria do not grow on the medium (circle, "○"); it changes to orange in the event of growing bacteria being $5 \times 10^6$ CFU/mL (triangle, "Δ"); or it changes to yellow when $1 \times 10^8$ CFU/mL (ex, "X").

The results are shown in Table 4. For all of the glasses treated under respective conditions, the medium assumes red color for 24 hours (○). From this, it is considered that growth inhibition is possible up to 24 hours after inoculation by antibacterial processing in any of the solutions. After 48 hours, growth inhibition is only observed in each solution of 3% EtAC+1% LAD and 3% EtAC+1% LAD+0.1% CPC using EtAC (○). Furthermore, after 90 hours, growth inhibition is only observed in the glass treated with 3% EtAC+1% LAD+0.1% CPC (○).

TABLE 4

| | | 24 hr | 48 hr | 90 hr |
|---|---|---|---|---|
| 1 | 3% Si—QAC + 1% PO + water | ○ | Δ | X |
| 2 | 3% Si—QAC + 1% PO + HD + water | ○ | Δ | X |
| 3 | 3% Si—QAC + 1% LAD + water | ○ | Δ | X |
| 4 | 3% EtAC + 1% LAD + water | ○ | ○ | X |
| 5 | 3% EtAC + 1% LAD + 0.1% CPC + water | ○ | ○ | ○ |

Example 5

Test 1 for Antibacterial Ability in 3 wt. % EtAC Aqueous Solution

The 60 wt. % EtAC ethanol solution obtained in Synthesis Example 1 is mixed with amphoteric surfactants and water, which are then prepared such that the final concentration of EtAC is 3% and the final concentration of the amphoteric surfactants 1%, respectively. CPB, Aromox and LAD are used as the amphoteric surfactants.

The resultant solutions are placed into a glass bottle, immersed for 20 minutes, removed and washed with water to remove excess solution, then left and dried for 3 hours, which is used in an experiment. Subsequently, 50 µL of bacterial suspension of $10^6$ CFU/mL *C. albicans* GDH18 is inoculated, left at room temperature for 12 hours, then added 3 mL of Sabouraud medium and cultured at 37° C. for 24 and 100 hours.

For the number of bacteria, a *Candida* yellow medium is used for simple calculation. The color of the medium remains red when bacteria do not grow on the medium (circle, "○"); it changes to orange in the event of growing bacteria being $5 \times 10^6$ CFU/mL (triangle, "Δ"); or it changes to yellow when $1 \times 10^8$ CFU/mL (ex, "X").

The results are shown in Table 5. For all of the glasses treated under respective conditions, the medium assumes red color for 24 hours (○). From this, it is considered that growth inhibition is possible up to 24 hours after inoculation by antibacterial processing in any of the solutions.

After 100 hours, as illustrated in Table 5, growth inhibition is observed in each solution added Aromox or LAD using EtAC (○).

TABLE 5

|   |                          | 24 hr | 100 hr |
|---|--------------------------|-------|--------|
| 1 | 3% EtAC + 1% Aromox + water | ○     | ○      |
| 2 | 3% EtAC + 1% LAD + water    | ○     | ○      |

Example 6

Test 2 for Antibacterial Ability in 3 wt. % EtAC Aqueous Solution

The 60 wt. % EtAC ethanol solution obtained in the Synthesis Example 1 is mixed with water and various surfactants and the stability is compared among them. The surfactants used are CPB, Aromox and LAD as amphoteric surfactants and PO as a non-ionic surfactant. The final concentration of EtAC is adjusted to 3 wt. % and the final concentration of each surfactant to 1 wt. %.

The resultant solutions are placed into a glass bottle, immersed for 20 minutes, removed and washed with water to remove excess solution, then left and dried for 3 hours, which is used in an experiment. Subsequently, 50 μL of bacteria suspension of $10^6$ CFU/mL C. albicans GDH18 (bacterial count: about 10,000) is inoculated and cultured at 37° C. for 18 hours.

Figure 2:
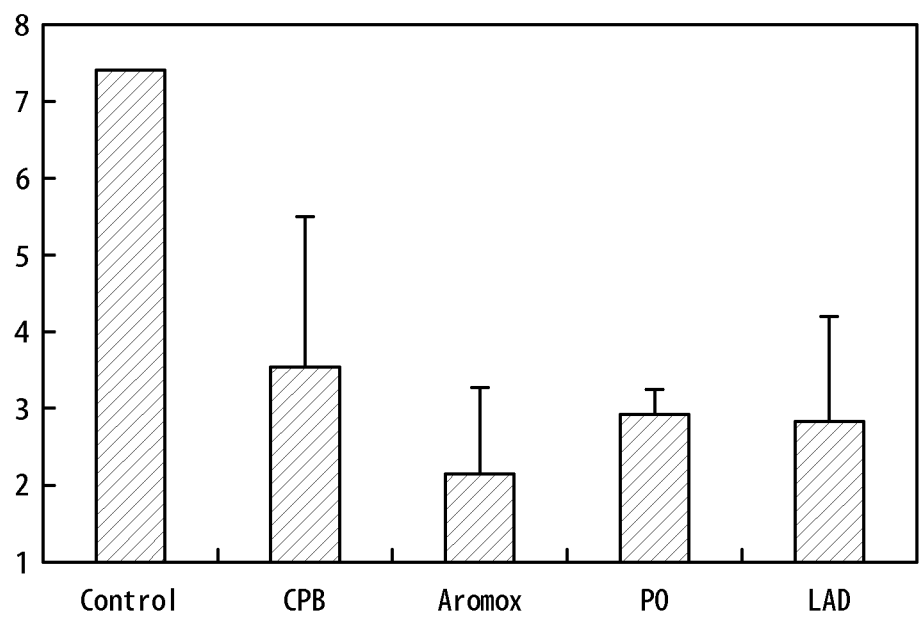
FIG. 2 is a graph depicting the result of an antibacterial ability test in an EtAC aqueous solution in Example 6, where the vertical axis represents the number of bacteria detected (logarithmic value)

For the number of bacteria, a Candida yellow medium is used for simple calculation. The results are shown in FIG. 2. The vertical axis of FIG. 2 represents the number of bacteria that are detected after being cultured for 18 hours (logarithm value). That is, if the vertical axis is 8, the number of bacteria present is 100,000,000; if the vertical axis is 6, the number of bacteria is 1,000,000. Any of these surfactants yield values lower than 4 of the number of inoculated bacteria (10,000 bacteria). It can be seen, however, that Aromox, in particular, yields 2 in logarithm value, namely around 100 bacteria, which may provide very high antibacterial abilities. This suggests a possibility that particularly EtAC and Aromox produce intermediates and thereby enhance the reactivity. Accordingly, upon analysis of the product in the above-described solution with FT-IR, production of intermediates is identified.

Example 7

Test for Antibacterialization of Hydroxyapatite

The 60 wt. % EtAC ethanol solution obtained in Synthesis Example 1 is mixed with Aromox and water, which is then prepared such that the final concentration of EtAC is 3% and Aromox 1%.

Sintered hydroxyapatite (Pentax APP-100) of 1 cm square (2 mm thick) is immersed in the resultant aqueous solutions for 5, 10, 20, 30 minutes, then removed and washed with water to remove excess solution, and left and dried for 1 hour, which is then used in an experiment.

Then, 20 μL of bacteria suspension of $10^6$ CFU/mL C. albicans GDH18 is inoculated, left at room temperature for 4 hours, then added 2 mL of Sabouraud medium and cultured at 37° C. for 24, 32 and 44 hours.

For the number of bacteria, a Candida yellow medium is used for simple calculation. The color of the medium remains red when bacteria do not grow on the medium (circle, "○"); it changes to orange in the event of growing bacteria being $5 \times 10^6$ CFU/mL (triangle, "Δ"); or it changes to yellow when $1 \times 10^8$ CFU/mL (ex, "X").

The results are shown in Table 6. For all of the hydroxyapatite treated under respective conditions, the medium assumes red color for 24 hours (○). From this, it is considered that growth inhibition is possible up to 24 hours after inoculation by antibacterial processing in any of the solutions. The bacteria growth of untreated hydroxyapatite (control) is about $5 \times 10^6$ CFU/mL (Δ).

For all of the hydroxyapatite treated under respective conditions, the medium assumes red color for 32 hours (○). From this, it is considered that growth inhibition is possible up to 32 hours after inoculation by antibacterial processing in any of the solutions. For the untreated hydroxyapatite (control), the medium assumes yellow color (X) and bacteria growth to be about $1 \times 10^8$ CFU/mL.

After 44 hours, bacterial growth is observed (Δ) for the hydroxyapatite subjected to immersion for five minutes, while no growth being observed (○) for others subjected to immersion for 10, 20, 30 minutes.

TABLE 6

|   | Immersion Time (min) | 24 hr | 32 hr | 44 hr |
|---|----------------------|-------|-------|-------|
| 1 | untreated            | Δ     | X     | X     |
| 2 | 5                    | ○     | ○     | Δ     |
| 3 | 10                   | ○     | ○     | ○     |
| 4 | 20                   | ○     | ○     | ○     |
| 5 | 30                   | ○     | ○     | ○     |

Example 8

Virus Inactivation Test

A test is performed to determine whether the detergent composition and the composition for disinfection, cleaning, mouth rinsing, sterilization and antibacterialization of the present invention have an ability to inactivate viruses. The viruses used are influenza virus and feline calicivirus (which belongs to the same genus as the human norovirus and is known to grow in CRFK cells of feline kidney cells, and which can be used as an alternative experimental system of human norovirus). Measurement of virus titer is performed by the 50% Tissue Culture Infectious Dose ($TCID_{50}$) method.

As a test solution, an 80% ethanol solution of 3 wt. % EtAC is prepared. A 10 cm² cell culture dish is used to culture canine kidney cells in the case of influenza virus and CRFK cells in the case of feline calicivirus to 70-100% confluent. Then, 100 μL of $100TCID_{50}$ influenza virus or feline calicivirus solution with 100 μL of test solution are added and placed in contact with 0.8 mL of 5% FCS-DMEM for 1 hour (as a result, viruses are diluted ten-fold to $10TCID_{50}$). Subsequently, 100 μL of 5% FCS-DMEM comprising virus is inoculated into 0.9 mL of cell culture liquid (5% FCS-DMEM), which is then cultured (as a result, viruses are diluted another 10-fold to $1TCID_{50}$). After 4-5 and 7-8 days, DMEM supplemented with 50 μL of 10% FCS is gently added to each well, respectively. After 11-13 days, a termination point of cytopathy is determined by a microscope. For each test solution and an untreated control using distilled water instead of each test solution, 50% tissue infectious rate ($TCID_{50}$) is calculated by the Reed-Muench method. As a result, 0.8-1.2 $TCID_{50}$ is obtained for the control (untreated), and the viral infection to the used culture cells is observed.

However, when treated with a solution containing EtAC, infection by any of viruses is not observed. From this, it is considered that the viruses are inactivated upon inoculation.

Example 9

Test for Virus Infection Inactivating Ability Against Influenza Virus

As influenza viruses, orthomyxoviridae influenza virus A A/swan/Shimane/499/83(H5N3) which is avian asymptomatic (an attenuated strain) and a atypical (swine) influenza virus (type H1N1) are used. They are purified by a sucrose density-gradient centrifugation and used as a virus liquid dialyzed against PBS. MDCK(+) cell which is a cell line of canine kidney cells is also used.

The above-described virus solution and the EtAC ethanol solution obtained in Synthesis Example 1 are mixed at a ratio of 1:9 (10 μL+90 μL), which is then reacted at room temperature for 3 minutes. From the processed virus liquid, 10-steps serial dilutions (including 0.6% EtAC, 0.2% EtAC, 0.06% EtAC, 0.02% EtAC, 0.006% EtAC, 0.002% EtAC, 0.0006% EtAC, 0.0002% EtAC, $6 \times 10^{-5}$% EtAC, 0% EtAC) are prepared with DMEM, inoculated into a monolayer cultured cell in a 96-well plate (50 μL/well), and subjected to a virus adsorption for 1 hour. The virus inoculated liquid is then removed by suction and DMEM, 20 μg/ml trypsin (100 μL/well) are added afterwards. This is fixed and stained upon spread of CPE after 5 days. Then, 50% tissue culture infectious rate (in TCID50) is calculated by the Behrens-Kaerber method to measure a virus-infectivity titer.

Figure 3:
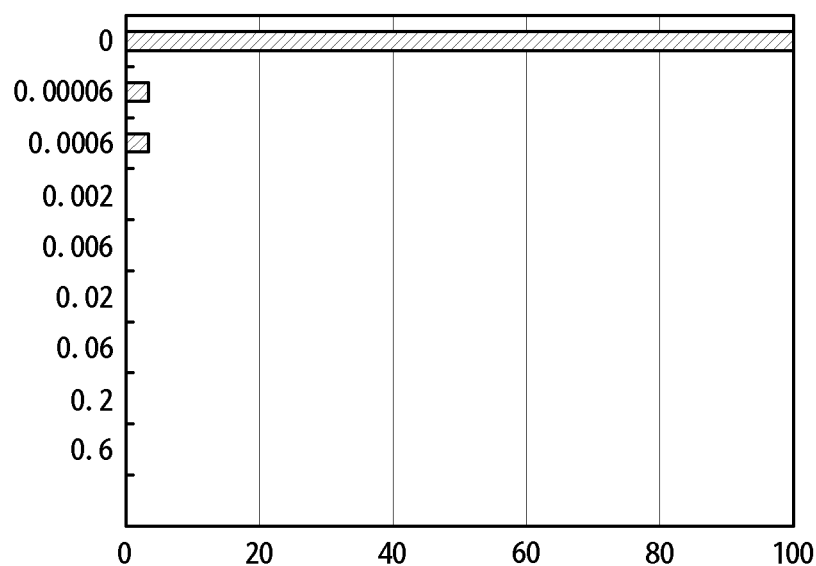
FIG. 3 is a graph depicting the result of a virus infection inactivating ability test against influenza virus in Example 9, where the vertical axis represents the concentration of EtAC (%) while the horizontal axis represents the amount of survival influenza viruses (%)
Figure 4:
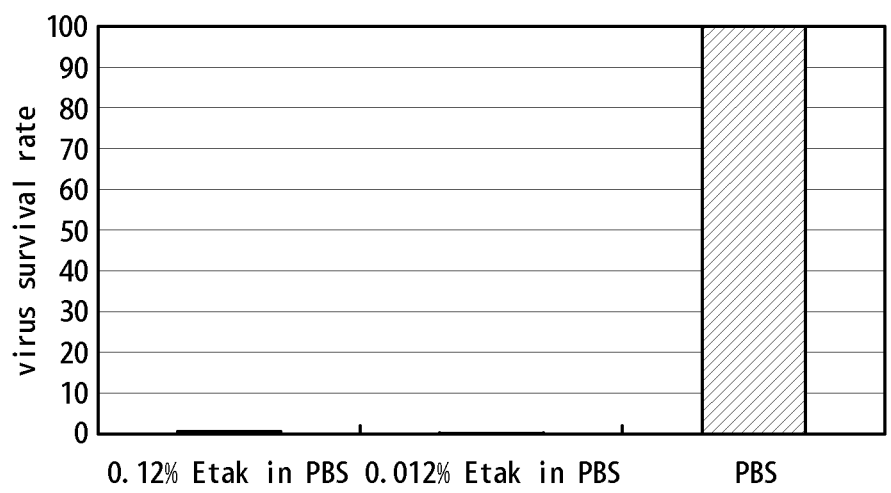
FIG. 4 is a graph depicting the result of a virus infection inactivating ability test against atypical (swine) influenza viruses (type H1N1) in Example 9, where the vertical axis represents the amount of survival influenza viruses (virus survival rate: %)

The results are reported in FIGS. 3 and 4. As illustrated in FIG. 3, it can be seen that when an EtAC ethanol solvent is diluted with DMEM, it is still effective if diluted to a residual infectivity titer of 0.002% (20 ppm). It should be noted that the above-described virus is an avian influenza attenuated strain, and the above-described virus liquid is a liquid that is purified by a sucrose density-gradient centrifugation and dialyzed against PBS, which results in less incorporation of impurities. In addition, as is the case with the results obtained for the avian influenza virus, highly significant effects are found for the atypical influenza virus (type H1N1) (see FIG. 4). It is assumed that these results are also common to the human type (H1N1, H3N2), type A influenza virus having the same physical properties as the avian influenza virus.

Example 10

Test for Anti-influenza Virus Action of EtAC-Treated Towel and EtAC-Treated Glass Vial The viruses (virus liquids) and cells used are the same as those used in Example 9.

The EtAC ethanol solution obtained in Synthesis Example 1 is diluted with ethanol for disinfection (80% ethanol) to prepare 80% ethanol solutions of 3 wt. % EtAC, 0.3 wt. % EtAC and 0.06 wt. % EtAC, which is then sprayed on a 100% cotton towel, left at room temperature for 3 minutes, then washed under running water and dried, by which an EtAC-treated towel is fabricated.

Then, about 17 mg of the resultant towel is weighed and placed into each well of a 24-well plate, which 50 μL of virus liquid is added dropwise and perfused. After the incubation at room temperature for 30 minutes, 300 μL DMEM (Dulbecco's modified Eagle's MEM) is added and viruses are collected with pipetting.

Then, the above 80 wt. % EtAC/ethanol solutions are adjusted to the concentrations of 0.3%, 0.15%, 0.1%, 0.75%, 0.06%, 0.03%, 0.01%, while the inner surface of the vial bottle is processed at room temperature for 10 minutes and then washed with ethanol four times and dried afterwards, by which an EtAC-treated glass vial is fabricated.

Then, the virus liquid (50 μL, or 50 μL virus liquid+250 μL DMEM) is placed into the resultant vial under shaking while incubating with a shaker for 30 minutes.

From the processed virus liquid, as is the case with Example 9, 10-steps serial dilutions are prepared with DMEM, inoculated into a monolayer cultured cell in a 96-well plate (50 μL/well), and subjected to a virus adsorption for 1 hour.

The virus inoculated liquid is then removed by aspiration, then DMEM and 20 μg/mL trypsin (100 μL/well) are added afterwards. This is fixed and stained upon spread of CPE after 5 days. Then, 50% tissue culture infectious dose (in TCID50) is calculated by the Behrens-Kaerber method to measure a virus-infectivity titer.

Figure 5:
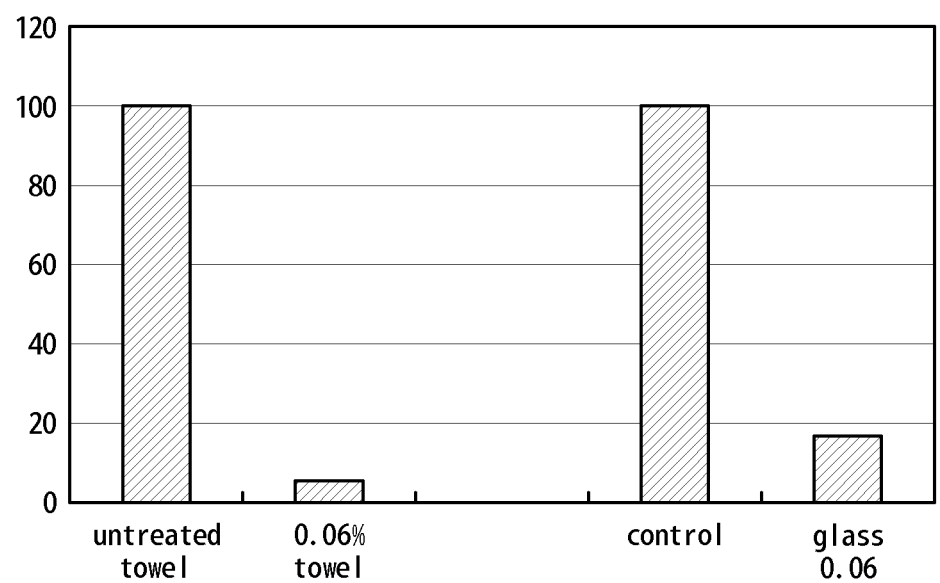
FIG. 5 is a graph depicting the result of an anti-influenza virus effect test of an EtAC-treated towel and an EtAC-treated glass vial in Example 10, where the vertical axis represents 50% infectious dose (tissue culture infectious dose [TCID50]).

The results are shown in FIG. 5. As illustrated in FIG. 5, it is found that both the EtAC-treated towel and EtAC-treated glass vial exhibit a very strong inactivation ability when treated at a concentration of 0.06% EtAC (80% ethanol solvent) or more.

The invention claimed is:

1. An antibacterial agent composition comprising:
a silicon-containing compound obtained from a compound of general formula (a):

$$X-(CH_2)_3-Si-(OCH_2CH_3)_3 \quad (a),$$

wherein X represents a halogen ion or an organic carbonyloxy ion, reacted in ethanol solvent to obtain a compound of general formula (1):

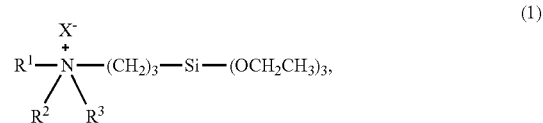

wherein $R^1$ represents an alkyl group having from 12 to 24 carbon atoms; $R^2$ and $R^3$ represent lower alkyl groups, respectively, having from 1 to 6 carbon atoms, and X represents a halogen ion or an organic carbonyloxy ion; ethanol;
water; and
an amphoteric surfactant and/or a cationic surfactant, wherein the cationic surfactant is cetylpyridinium chloride, N-cocoyl-alginine ethyl ester pyridone carboxylate, or a cationic surfactant represented by general formula (2):

wherein $R^{11}$ represents a hydrocarbon group having 6 or more carbon atoms; $R^{12}$, $R^{13}$ and $R^{14}$ represent lower hydrocarbon groups, respectively, and Y represents a halogen ion or an organic carbonyloxy ion, the content of the silicon-containing compound represented by the compound of formula (1) in the antibacterial agent composition is 0.006-24 wt. %, and the content of the ethanol in the antibacterial agent composition is 35-85% by volume.

2. The antibacterial agent composition according to claim 1, wherein the silicon-containing compound represented by the general formula (1) is octadecyldimethyl(3-triethoxysilylpropyl) ammonium chloride.

3. An antibacterializing method comprising contacting a surface of an article with the antibacterial agent composition according to claim 1.

4. A cleaning/mouth rinsing method comprising cleaning/mouth rinsing with the antibacterial agent composition according to claim 1.

5. An article of manufacture made by a process comprising: applying or spraying the antibacterial agent composition according to claim 1 onto a surface of an article having oxygen-containing functional groups on its surface, or immersing the article in the antibacterial agent composition according to claim 1.

6. A method for fixing an antibacterial agent, comprising: applying or spraying the antibacterial agent composition according to claim 1 onto the surface of an article having oxygen-containing functional group on its surface, or immersing the article in the antibacterial agent composition according to claim 1.

7. An antiviral agent composition comprising:

a silicon-containing compound represented by general formula (1):

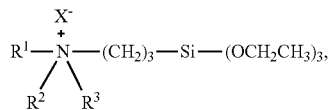

(1)

wherein $R^1$ represents an alkyl group having 12-24 carbon atoms; $R^2$ and $R^3$ are lower alkyl groups having 1-6 carbon atoms; and X is a halogen ion or an organic carbonyloxy ion;

ethanol; and an amphoteric surfactant and/or a cationic surfactant, wherein the cationic surfactant is cetylpyridinium chloride, N-cocoyl-alginine ethyl ester pyridone carboxylate, or a cationic surfactant represented by general formula (2):

(2)

wherein $R^{11}$ represents a hydrocarbon group having 6 or more carbon atoms; $R^{12}$, $R^{13}$ and $R^{14}$ represent lower hydrocarbon groups, respectively; and Y represents a halogen ion or an organic carbonyloxy ion, the content of the silicon-containing compound represented by the formula (1) in the antiviral agent composition is 0.006-24 wt. %, and the content of the ethanol in the antiviral agent composition is 35-85% by volume.

8. The antiviral agent composition according to claim 7, wherein the silicon-containing compound represented by the general formula (1) is octadecyldimethyl(3-triethoxysilylpropyl) ammonium chloride.

9. The antiviral agent composition according to claim 7 further comprising water.

10. The antiviral agent composition according to claim 7, wherein said composition inactivates at least one type of virus selected from the group consisting of: type A influenza virus, type B influenza virus, parainfluenza virus and norovirus.

11. A method for fixing an antiviral agent, comprising: applying or spraying the antiviral agent composition according to claim 7 onto the surface of an article having oxygen-containing functional group on its surface, or immersing the article in the antiviral agent composition according to claim 7.

* * * * *